United States Patent [19]

Aviv et al.

[11] Patent Number: 5,496,811
[45] Date of Patent: Mar. 5, 1996

[54] SUBMICRON EMULSIONS AS OCULAR DRUG DELIVERY VEHICLES

[75] Inventors: Haim Aviv, Rehovot; Doron Friedman, Carmei Yossef; Amir Bar-Ilan, Neve Monsson; Micha Vered, Rehovot, all of Israel

[73] Assignee: Pharmos Corp., New York, N.Y.

[21] Appl. No.: 854

[22] Filed: Jan. 5, 1993

[30] Foreign Application Priority Data

Aug. 28, 1992 [IL] Israel ......................................... 102984
Nov. 27, 1992 [IL] Israel ......................................... 103907

[51] Int. Cl.$^6$ .......................... A61K 31/685; A61K 31/66; A61K 31/22; A61K 31/225
[52] U.S. Cl. ................... 514/78; 514/75; 514/76; 514/546; 514/547; 514/560; 514/912
[58] Field of Search .................. 514/76, 75, 78, 514/912, 546, 547, 560

[56] References Cited

U.S. PATENT DOCUMENTS 4,289,080  9/1981  Penley ...................................... 198/470
4,914,088  4/1990  Glonek et al. .............................. 514/76

FOREIGN PATENT DOCUMENTS

0028110A3  5/1981  European Pat. Off. ..
0253472A1  1/1988  European Pat. Off. ..
0391369A2  10/1990 European Pat. Off. ..
0480690A1  4/1992  European Pat. Off. ..

OTHER PUBLICATIONS

Hardberger, R., "Effects of Drug Vehicles on Ocular Contact Time", 93:42–45 (1975).

*Primary Examiner*—Zohreh Fay
*Attorney, Agent, or Firm*—Pennie & Edmonds

[57] ABSTRACT

An ocular drug delivery vehicle of an oil-in-water submicron emulsion comprising about 0.5 to 50% of a first component of an oil, about 0.1 to 10% of a second component of an emulsifier, about 0.05 to 5% of a non-ionic surfactant and an aqueous component, with the mean droplet size being in the submicron range, i.e., below about 0.5 μm and preferably between about 0.1 and 0.3 μm. Also, topical pharmaceutical compositions containing a drug such as an anti-glaucoma drug, beta adrenergic blocker or other autonomic system drug, a local anesthetic, a steroid, a non-steroidal anti-inflammatory drug, an antibiotic drug, an antifungal drug, an antiviral drug or combinations thereof and the vehicle described above. Methods of administering such vehicles or compositions to the eye of a patient while reducing irritation thereof and providing increased bioavailability of the drug.

37 Claims, 3 Drawing Sheets

SUBMICRON EMULSIONS AS OCULAR DRUG DELIVERY VEHICLES

FIELD OF THE INVENTION

The present invention relates to the field of drug delivery and, particularly, to the administration of various pharmaceutical agents to a patient through the eye by application of the innovative compositions of these agents in a non-irritating submicron emulsion.

BACKGROUND OF THE PRESENT INVENTION

The primary problem associated with topical applications of drugs to the eye is that the human eye is a very sensitive organ and any substance which is not compatible with it causes irritation and pain. This evokes blinking and reflex-tearing, which is a physiological reaction intended for removal of the irritating substance from the ocular surface. Irritation is a major cause of poor patient compliance with many ophthalmic drugs. This phenomenon is aggravated by the need to include relatively high concentrations of a drug in such ophthalmic compositions in order to obtain a therapeutic effect, since bioavailability of topically applied ophthalmic drugs is generally very poor. Thus, there is no doubt that a reduction in the irritating effect of a drug will enable increased ocular drug bioavailability, increased patient compliance with the drug, and enhanced therapeutic efficacy of the drug.

Currently, aqueous solutions are by far the most common vehicles for ophthalmic drugs. Such vehicles have a serious drawback, however, in that the ocular bioavailability of drugs administered thereby is generally very poor due to rapid drainage and tear turnover. See Fitzgerald et al. (1987) J. Pharm. Pharmacol. 39:487–490. A typical dose of ophthalmic solution is in the range of about 50–100 µl, which far exceeds the normal lachrymal volume of about 7–10 µl. Thus, the portion of the dose that is not eliminated by spillage from the pulberal fissure is quickly drained. Furthermore, lachrymation and physiological tear turnover, which in humans is about 16% per minute under normal conditions, increases after the introduction of the solution, resulting in rapid dilution of the remaining amount of drug that has not been spilled or drained. As a consequence, the contact time with the absorbing surfaces of the eye (i.e., the cornea and sclera) of drugs which are applied to the eye via liquid aqueous compositions is less than about two minutes.

Another drawback of aqueous vehicles is that many drugs which may potentially be used in eye therapy are hydrophobic and their delivery into the eye by such aqueous vehicles is not possible. While such hydrophobic drugs may potentially be administered to the eye in conjunction with various organic solvents, the use of such solvents usually causes irritation and inflammatory reactions. See Harmia et al. (1987) Pharm. Acta Helv. 62:322–332.

Attempts have been made to develop various delivery vehicles in which the drug residence time in the eye is increased. The most direct approach for achieving this goal is by an increase in the viscosity of the vehicle. Thus, various viscous vehicles, such as hydrogels or ointments, have been attempted, some of which also enable delivery of hydrophobic drugs into the eye. Additionally, many attempts to use various non-conventional carriers, such as liposomes, micellar solutions and nanoparticles, as vehicles of ophthalmic drugs have also been made. While the use of such delivery systems may provide limited success in prolonging the residence time of drugs in the eye and hence some enhancement of the ocular bio-availability, such carriers also produce various deleterious side effects. See Harmia et al., supra., Saettone et al. (1988) J. Pharm. 43:67–70 and Meisner et al. (1989) Int. J. Pharm. 55:105–113.

Emulsions have also been suggested as vehicles for delivery of drugs to the eye in references such as EP 391,369, Ellis et al. (1987) J. Ocular Pharmcol. (U.S.) 3:121–128, and Shell (1984) Surv. Ophthalmol. 29:177–178. Nevertheless, the practical inability to realize the potential of emulsion systems for ocular drug delivery stems predominantly from two problems. First, ocular drug formulations must be comfortable to the patient as well as safe, due to the sensitivity of the delicate eye tissues involved. Second, emulsions are generally metastable dispersions of immiscible fluids and these instability problems must be overcome.

An emulsion is a dispersion of oil in water ("o/w"), and can be defined as either a macroemulsion or a microemulsion. A macroemulsion is a cloudy turbid composition having an oil-droplet size of 0.5 to 100 µm and is generally thermodynamically unstable. In comparison, a microemulsion is a translucent to transparent composition having a droplet size of 0.005 to 0.5 µm, is thermodynamically stable and is generally self emulsifying. See, e.g., Friberg et al. (1987) Microemulsions Structure and Dynamics, CRC Press Inc., Boca Raton, Fla., pp. 154. Also, the proportion of surfactants to oil required to generate microemulsions is generally much higher than in macroemulsions.

Emulsions developed specifically for ophthalmic use have attempted to solve the problem of inherent instability through the use of microemulsions or the addition of stabilizing polymers to classical emulsions. In several instances, specific drugs have been formulated successfully in microemulsions. Examples of this approach include ophthalmic microemulsions of tepoxalin, as disclosed in EP 480,690, or flurbiprofen, as disclosed in EP 253,472.

An alternative approach to solve the problem of emulsion instability utilizes lightly crosslinked polymers, as exemplified by the autoclavable emulsions for ophthalmic use which are disclosed in EP 028,110.

In addition, the use of emulsions in ophthalmic preparations has been limited to a large extent by the inclusion of surfactants in the emulsions which surfactants are highly irritating to the eye. For example, the use of the emulsion preparations of EP 391,369 are limited considerably by the irritating effect of the ionic surfactants which are used in those emulsions. Thus, to date no commercially successful ophthalmic compositions in the form of oil-in-water emulsions are available.

The present invention solves the problem of emulsion instability without resorting to either of the prior art suggestions by instead converting classical emulsions to submicron emulsions with the input of energy by shear forces and homogenization to provide submicron emulsions possessing substantially reduced eye irritation properties. Also, the irritation of the eye is further reduced through the use of non-irritating non-ionic surfactants in such emulsions. Thus, when drugs are included with these submicron emulsions, the present invention provides ophthalmic compositions which are improved over those which are currently available in the art. In accordance with the present invention, effective means for reducing irritation of the eye, particularly such irritation which is drug-induced, is provided for the first time and thereby a long felt need has been fulfilled.

SUMMARY OF THE INVENTION

The present invention provides an ocular drug delivery vehicle of an oil-in-water submicron emulsion comprising about 0.5 to 50% of a first component of an oil, about 0.1 to 10% of a second component of an emulsifier, about 0.05 to 5% of a non-ionic surfactant and an aqueous component, with the mean droplet size being in the submicron range, i.e., below about 0.5 μm and preferably between about 0.1 and 0.3 μm.

The first component may be a medium chain triglyceride oil, a vegetable oil, a mineral oil or mixtures thereof, and is usually present in an amount of about 1 to 20%. For viscous compositions or creams, the oil may be present in an amount of about 30 to 50%.

The emulsifier is preferably a phospholipid compound or a mixture of phospholipids, such as lecithin, phosphatidylcholine, phosphatidyl ethanolamine or mixtures thereof, and is preferably present in an amount of about 0.2 to 1%.

The surfactant is preferably a non-ionic alkylene oxide condensate of an organic compound which contains one or more hydroxyl groups, such as an ethoxylated alcohol or ester compound, and is preferably present in an amount of about 0.2 to 1%.

This vehicle may be used to prepare topical ophthalmic compositions which include an effective amount of an ophthalmic drug. In these compositions, the drug can be an anti-glaucoma drug, such as a beta adrenergic blocker or other autonomic system drugs, a local anesthetic, asteroid, a non-steroidal anti-inflammatory drug, an antibiotic drug, an antifungal drug, an antiviral drug or combinations thereof. Moreover, the drug may be hydrophilic or amphiphilic, such as pilocarpine or timolol, or hydrophobic, such as indomethacin, betaxolol or adaprolol. The drug is typically present in an amount of about 0.05 to 5% by weight depending upon the specific drug to be used. If desired, these compositions may also include a preservative, an antioxidant or an osmotic agent such as an osmotic pressure regulator.

The present invention also provides a method for reducing eye irritation which comprises topically administering to the eye the oil-in-water submicron emulsion described above. A particular aspect of this embodiment of the present invention is the combined topical administration to the eye of the submicron emulsion defined above and an effective amount of a drug, in order to reduce irritation which may otherwise be induced by the drug. This enables increased amounts of the drug to be administered without irritation.

BRIEF DESCRIPTION OF THE DRAWINGS

In the following detailed description of the invention, reference will be made to the annexed drawings, in which.

DETAILED DESCRIPTION OF THE INVENTION

The present invention has for the first time achieved emulsions effective as a general drug delivery vehicle for ophthalmological use. The present invention provides stable pharmaceutical preparations which are oil-in-water emulsions having droplets or colloidal particles of a submicron size and utilizing surfactants that are non-ionic.

The ingredients in the composition of the present invention are preferably those which are compatible physiologically with the eye, i.e., those which do not cause irritation to the eye by themselves. The judicious optimization of such ingredients enables reduced irritation of commonly used ophthalmic drugs, while simultaneously providing enhanced bioavailability of certain drugs. In parallel, the intrinsic problems of instability of drug containing emulsions have been solved by providing the droplet size of the oil phase in the submicron range.

The term "submicron" is used herein to mean a size of about 0.05 to 0.5 μm, and preferably about 0.1 to 0.3 μm. Thus, a submicron emulsion having droplets of these sizes would be smaller than those of a classical macroemulsion, which has droplet sizes of above 0.5 μm, but generally larger than those of a classical microemulsion, which, for practical purposes, has droplet sizes of less than 0.1 μm.

These submicron emulsion can easily be sterilized by filtration, for example, in 0.45 μm and/or 0.22 μm filters, are more stable in long-term storage and can better withstand sterilization in an autoclave.

An oil-in-water emulsion is a dispersion of droplets or colloidal particles in an aqueous medium, with the colloid particles having an oily core surrounded by an interfacial film of the emulsifiers and surface acting agents or surfactants. For clarity in understanding the present invention, the following terms will be used:

"aqueous phase"—to denote the aqueous solution in which the droplets or colloid particles are dispersed;

"oily phase"—to denote the oily cores of the droplets or colloidal particles; and "amphiphilic phase"—to denote the interfacial films of emulsifier and surfactant surrounding the oily phase of the droplets or colloidal particles.

These colloidal particles have a soothing effect on the eye by a physiological mechanism which has not yet been elucidated. Owing to this soothing effect, the topical ophthalmic compositions of the invention having a certain drug concentration will have a smaller irritating effect than a prior art composition having the same drug concentration. This is surprisingly the case both with respect to hydrophilic and hydrophobic drugs. The surprising fact that the soothing and irritation reducing effect occurs also where the drug is hydrophilic, i.e. water soluble, shows that the reduced irritation does not result merely by containment of the drug in the colloid particles but rather by some other mechanism.

The present invention is useful for reducing drug-induced irritation of various anti-glaucoma drugs, such as beta-adrenergic blockers or other autonomic system drugs, anesthetics, steroids, non-steroidal anti-inflammatory drugs, antibiotic drugs, anti-fungal drugs, antiviral drugs or combinations thereof. The term "effective amount" is used herein to denote an amount of a drug which is effective in exerting a pharmaceutical affect on the eye.

A number of exemplary drugs which are known to induce irritation were tested in accordance with the invention, and in all cases the drug-induced irritation was considerably reduced when the drugs were administered together with the above colloid particles. These drugs include the water soluble drugs timolol and pilocarpine. Pilocarpine, 3-ethyldihydro- 4-[(1-methyl-1H-imidazole-5-yl)methyl]- 2(3H)-furanon, is a drug which is soluble in water and sparingly soluble in oil, which is used in the treatment of glaucoma. Also, water insoluble drugs, such as indomethacin, betaxolol and adaprolol (adaprolol being an experimental soft beta blocker disclosed in U.S. Pat. No. 4,289,080), can be used. Owing to the reduced irritability, compositions of the present invention may contain higher concentrations of drugs than prior art compositions.

The oily phase comprises an oil which may be a vegetable oil, a mineral oil, a medium chain triglyceride (MCT) oil, i.e. a triglyceride oil in which the carbohydrate chain has 8–12 carbons, or a combination of two or three of such oils. Although MCT oil can be considered as a component of vegetable oil, it is separately identified herein because of its particular utility as a preferred oil for use in the present emulsions. In addition, MCT oil is available commercially. Examples of such MCT oils include TCR (trade name of Societe Industrielle des Oleagineaux, France for a mixture of triglycerides wherein about 95% of the fatty acid chains have 8 or 10 carbons) and MIGLYOL 812 (trade name of Dynamit Nobel, Sweden for a mixed triester of glycerine and of caprylic and capric acids). Examples of vegetable oils include soybean oil, cotton seed oil, olive oil, sesame oil and castor oil. The mineral oils may be natural hydrocarbons or their synthetic analogs. Oily fatty acids, such as oleic acid and linoleic acid, fatty alcohols, such as oleyl alcohol, and fatty esters, such as sorbitan monooleate and sucrose mono- di- or tri-palmitate, can be used as the oil component, although these are not as preferred as the other oils mentioned above.

The amphiphilic phase comprises the emulsifiers and surfactants. Preferred emulsifiers include a phospholipid compound or a mixture of phospholipids. Suitable components include lecithin; EPICURON 120 (Lucas Meyer, Germany) which is a mixture of about 70% of phophatidylcholine, 12% phosphatidylethanolamine and about 15% other phospholipids; OVOTHIN 160 (Lucas Meyer, Germany) which is a mixture comprising about 60% phosphatidylcholine, 18% phosphatidylethanolamine and 12% other phospholipids; a purified phospholipid mixture; LIPOID E-75 or LIPOID E-80 (Lipoid, Germany) which is a phospholipid mixture comprising about 80% phosphatidylcholine, 8% phosphatidylethanolamine, 3.6% non-polar lipids and about 2% sphingomyelin. Purified egg yolk phospholipids, soybean oil phospholipids or other purified phospholipid mixtures are useful as this component. This listing is representative and not limiting, as other phospholipid materials which are known to those skilled in the art can be used.

The surfactant chosen should be non-ionic and one skilled in the art can conduct tests to routinely select specific surfactants which induce minimal (and preferably no) irritation of the eye. Generally, the surfactant is a non-ionic alkylene oxide condensate of an organic compound which contains one or more hydroxyl groups. For example, ethoxylated and/or propoxylated alcohol or ester compounds or mixtures thereof are commonly available and are well known to those skilled in the art. Suitable surfactants include, but are not limited to, TYLOXAPOL; POLOXAMER 4070; POLOXAMER 188; POLYOXYL 40 Stearate; POLYSORBATE 80, and POLYSORBATE 20, as well as various compounds sold under the trade name TWEEN (ICI American Inc., Wilmington, Del. U.S.A.), PLURONIC F-68 (trade name of BASF, Ludwigshafen, Germany for a copolymer of polyoxyethylene and polyoxypropylene). The TYLOXAPOL and TWEEN surfactants are preferred because they are FDA approved for human use.

The aqueous component will be the continuous phase of the emulsion and may be water, saline or any other suitable aqueous solution which can yield an isotonic and pH controlled preparation.

In addition, the compositions of the invention may also comprise conventional additives such as preservatives, osmotic agents or pressure regulators and antioxidants. Typical preservatives include Thimerosal, chlorbutanol, and methyl, ethyl, propyl or butyl parabens. Typical osmotic pressure regulators include glycerol and mannitol, with glycerol being preferred. The preferred oil phase antioxidant is $\alpha$-tocopherol or $\alpha$-tocopherol succinate. The aqueous phase may also include an antioxidant of a polyamine carboxylic acid such as ethylene diamino tetraacetic acid, or a pharmaceutically acceptable salt thereof.

If desired, the compositions of the present invention may also include additional drugs which are effective in decreasing the intraocular pressure of the eye. Such drugs may for example be $\beta$-adrenergic blockers, cannabinoids, cholinesterase inhibitors, sympathomimetic agents or carbonic anhydrase inhibitors.

In the following description, concentrations will be indicated by % which denotes the concentration by weight of the component per 100 units volume of entire composition. All indicated concentrations should be understood as standing each by itself, and not cumulative. It should be appreciated by the artisan, however, that there is some dependency between the concentrations of the components, e.g., higher concentrations of the oil will generally require higher concentrations of the emulsifier and surfactant.

The emulsion used in the ophthalmic compositions of the present invention may comprise about 0.5 to 50% oil, about 0.1 to 10% emulsifier and about 0.05 to 5% surfactants. Generally, increasing the concentration of the non-aqueous phase, i.e., the combined concentration of the oily and the amphiphilic phase, increases viscosity of the composition. In order to obtain a non-viscous composition, the concentration of the non-aqueous phase should generally not exceed about 25%.

Preferred concentrations of the components are as follows: about 1 to 20% oil, most preferably about 1 to 10% for a composition intended to be fluid, or about 30 to 50% for a viscous composition which may be useful as a cream or ointment; about 0.2 to 5% of the emulsifier, with about 0.2 to 1% being particularly preferred; and about 0.2 to 5% for the surfactant, with about 0.2 to 1% being particularly preferred.

The drug is present in an amount of about 0.05 to 5% by weight of the composition, preferably about 0.1 to 2.5%. Depending upon whether the drug is hydrophilic or hydrophobic, it will be physically present in the oily phase or the aqueous component. Also, the pH of these compositions should be in a range which is suitable for the stability of the drug, but as close to neutral as possible for compatibility with the eye.

The present invention is also based on the surprising finding that the colloidal particles of the oil-in-water emulsions disclosed herein have a soothing and irritation reducing effect on the eye. Thus, where a drug which otherwise causes an irritating effect on the eye is administered together with such colloidal particles, the irritation which would have otherwise occurred, is reduced considerably. The soothing effect of the composition of the present invention also occurs where an emulsion without a drug is administered to an already irritated eye. Thus, the submicron emulsions of the present invention are useful for reducing drug-induced irritation of a number of pharmaceuticals.

EXAMPLES

The present invention will now be illustrated with reference to several non-limiting embodiments described in the following examples, which utilize the following ingredients:

MCT oil: TCR—Societe Industrielle des Oleagnieux, St. Laurent, Blangy, France.

LIPOID E-75 or E-80: Lipoid, Ludwigshafen, Germany.

α-tocopherol, α-tocopherol succinate and glycerol: Sigma, St. Louis, Mo., U.S.A., in conformity with U.S.P. specifications.

Pilocarpine base: Merck, Darmstadt, Germany, in conformity with U.S.P. and B.P.

EDTA: ethylene diamine tetraacetate disodium dihydrate).

Example 1: A blank oil-in-water type emulsion (without a drug) was prepared from the following ingredients:

| | |
|---|---|
| MCT (medium chain triglyceride) oil | 4.25% |
| LIPOID E-75 | 0.75% |
| TYLOXAPOL (a non-ionic surfactant) | 1.0% |
| α-tocopherol (an oil phase antioxidant) | 0.02% |
| EDTA (an aqueous phase antioxidant) | 0.1% |
| Preservatives (antibacterial) | |
| Chlorbutanol | 0.2% |
| Thimerosal | 0.01% |
| Glycerol (an osmotic agent) | 2.25% |
| Distilled water | balance to 100.00% |

The emulsion was prepared as follows:

The aqueous and oily phases were separately prepared. The aqueous phase consisted of water, tyloxapol, chlorbutanol, thimerosal and glycerol; and the oily phase consisted of the MCT oil, lecithin and α-tocopherol. The pH of the aqueous phase was adjusted to pH 6.8 and the two phases were filtered (TE and BA filter types, Schleicher & Schull, Dassel, Germany, having a pore size of 0.22 μm). Next, the two phases were heated separately to over 50° C. and then were combined and stirred with a magnetic stirrer to produce a coarse emulsion. The mixture was further heated to a temperature of 80°–85° C. The coarse emulsion was further mixed by a high-shear mixer, POLYTRON (Kinematica, Switzerland), for 3 minutes, and then was rapidly cooled to below 40° C. After cooling, the emulsion was homogenized by a 2-stage homogenizer (APV Montin Gaulin, Germany) at 8000 psi and then cooled again to storage (i.e., room) temperature. After adjusting the pH to 6.8–7, the emulsion was filtered through a membrane filter (TE, Schleicher & Schull, having a pore size of 0.45 μm) and transferred to plastic bottles that were sealed under nitrogen atmosphere. The emulsions were then sterilized either by a steam autoclave at 121° C. or by a double stage membrane filtration, through a 0.45 μm filter followed by a 0.22 μm filter (i.e., TE filters manufactured by Schleicher & Schull). The final preparation had an osmolarity of 298 mOsmol/1 and an initial pH of 6.47.

Examples 2–5: Pilocarpine Compositions

This composition had the same constituents as the composition of Example 1 above, except with the addition of 1.7% pilocarpine base (2% as Pilo-HCl). In the preparation process, pilocarpine was added to the aqueous phase and the solutions were mixed at about 50° C. due to the heat sensitivity of the drug. The resulting composition had an initial pH of 5 and an osmolarity of 278 mOsmol/1.

Three additional pilocarpine compositions were prepared as above except that they contained 1.5% TYLOXAPOL, 1% TWEEN-80 and 1% TWEEN-20, respectively.

Examples 6–8: Adaprolol Maleate Compositions

This composition had the following constituents:

| | |
|---|---|
| Adaprolol maleate | 0.4% |
| MCT oil | 4.25% |
| LIPOID E-80 | 0.75% |
| TWEEN-80 | 1.0% |
| α-tocopherol | 0.02% |
| EDTA | 0.1% |
| Glycerol | 2.2% |
| Distilled water | balance to 100.00% |

The composition was prepared in a similar manner to that described above in Example 1 except that adaprolol was added during preparation to the oil phase. The resultant composition had an initial pH of 6.5 and an osmolarity of 338 mOsmol/1.

Two additional adaprolol compositions were prepared as above except that they contained 1 TYLOXAPOL and 1% TWEEN-20, respectively.

Example 9: Betaxolol Composition

This composition had the following constituents:

| | |
|---|---|
| MCT oil | 4.25% |
| LIPOID E-80 | 0.75% |
| TWEEN-80 | 0.5% |
| α-tocopherol succinate | 0.02% |
| Betaxolol | 0.5% |
| Glycerol | 2.2% |
| Distilled water | balance to 100.00% |

The manner of preparation was the same as that of the adaprolol compositions of Examples 6–8 above.

Examples 10–11: Indomethacin Compositions

This composition had the following constituents:

| | |
|---|---|
| Indomethacin | 0.4% |
| MCT oil | 17% |
| LIPOID E-80 | 3% |
| TWEEN-80 | 1% |
| α-tocopherol succinate | 0.02% |
| Methyl paraben | 0.1% |
| Propyl paraben | 0.02% |
| Glycerol | 2.25% |
| EDTA | 0.1% |
| Distilled water | balance to 100.0% |

A second composition (Example 11) was made similar to that of Example 10, except that it contained 0.2% of indomethacin. The manner of preparation was the same as that of the adaprolol composition of Example 6 above. The initial pH of these compositions was about 5.

Examples 12–13: Ocular Irritation Tests

Acute irritative response and long term irritative response of animal eyes to various ophthalmic preparations were tested as follows:

Example 12: Acute Irritative Response Tests

The acute response was quantified using the guinea pig blinking test. In this test, the number of blinks during a 5 minute period was counted in 0.5 minute increments following application of a 25 µl drop of test solution. Each eye was first tested with normal saline (0.9% NaCl) and then with the test formulation, with at least a 30-minute interval between the two tests. The number of blinks of both eyes of each animal was averaged and entered as a single value. Two parameters were calculated from the data thus obtained:

Maximal Blinking Ratio (MBR): The highest number of blinks, counted during an 0.5 minute period, following drug application, divided by the highest number of blinks, in an 0.5 minute period, following saline treatment.

$$MBR = \frac{\text{maximum blinks} - \text{drug}}{\text{maximum blinks} - \text{saline}}$$

MBR represents the maximal measured response to the drug and is thought to be equivalent to the burning or stinging response described by human subjects.

Blinking Index (BI): The number of blinks, counted during the entire 5 minute observation period, following drug treatment, divided by the number of blinks counted during the 5 minute period following saline treatment.

$$BI = \frac{\text{number of blinks} - \text{drug}}{\text{number of blinks} - \text{saline}}$$

BI incorporates both the maximal response and its duration and is thought to be indicative of the drug induced irritation. Results are shown in Table 1.

TABLE 1

| | Acute Irritative Response | | | |
|---|---|---|---|---|
| | Aqueous solution | | SME formulation | |
| Test compound | MBR | BI | MBR | BI |
| Blank (saline) | — | 1.0 ± 0.3 | — | 0.7 ± 0.4* |
| Pilocarpine HCl 2% (Mi-Pilo Fischer) | — | 2.1 ± 0.7 | 1.1 ± 0.7 | 1.4 ± 0.5* |
| Adaprolol 0.4% | 4.9 ± 2.4 | 3.5 ± 0.9 | 0.9 ± 0.3* | 1.6 ± 0.4* |
| Timolol Maleate 0.5% (Tiloptic) | 3.7 ± 2.5 | 2.2 ± 0.7 | 1.8 ± 0.7* | 1.8 ± 0.8 |
| Betaxolol 0.5% (Betoptic) | 1.5 ± 0.4 | 1.6 ± 0.4 | 1.6 ± 1.2 | 1.5 ± 0.3 |

Means ± S.D. (n = 10 animals)
*Submicron emulsion significantly differs from aqueous solution at P < 0.05.

Example 13: Long Term Irritative Response Tests

These effects were quantified in albino NZW rabbits by the Draise Test (c.f., Draise (1944) J. Pharmacol. Exp. Ther. 83:377–390) using slit-lamp biomicroscopy. The irritative responses of the ocular surface, i.e., conjunctiva erythema (on a scale of 0–3), discharge (on a scale of 0–3), and corneal fluorescein staining (on a scale of 0–4), were graded following topical treatment using standardized scales. The effects were studied during a 5 day period with 4 drops/day being administered. Assessment of irritation was done after 2, 6, 9, 13 and 18 drops. The scores obtained in each category (i.e., conjunctiva, cornea, etc.) were combined to form one irritative index, with the maximum score being 10. The results which were obtained are shown in Table 2.

TABLE 2

| | Long Term Irritative Response | | | | |
|---|---|---|---|---|---|
| | Irritative index No. of treatment (drops) | | | | |
| Treatment | 2 | 6 | 9 | 13 | 18 |
| Emulsion alone | 1.0 ± 0.8 | 0.2 ± 0.2 | 0.4 ± 0.3 | 0.2 ± 0.2 | 0.9 ± 0.5 |
| Adaprolol 0.4% (aqueous sol.) | 3.0 ± 0.9 | 3.9 ± 0.6 | 3.1 ± 0.8 | 3.2 ± 0.8 | 3.6 ± 0.7 |
| Adaprolol 0.4% Emulsion | 1.5 ± 1.0* | 2.0 ± 1.0 | 1.7 ± 0.6* | 1.8 ± 0.7* | 2.7 ± 1.5* |
| Timoptic 0.5% Timolol Maleate | 1.4 ± 0.9 | 2.3 ± 0.8 | 0.9 ± 0.2 | 2.3 ± 0.9 | 1.1 ± 0.7 |
| Timolol Maleate 0.5% Emulsion | 0.6 ± 0.4* | 1.1 ± 0.7* | 1.0 ± 1.0 | 1.4 ± 1.2* | 0.7 ± 0.8* |

Means ± S.D. n = 12 eyes
*Submicron emulsion formulations significantly differ at P < 0.05 from buffer/aqueous formulation These results clearly show that drugs administered with the submicron emulsion formulations of the present invention were much less irritating than drugs administered in standard formulations, whether the drug is hydrophilic such as pilocarpine or timolol and whether the drug is hydrophobic such as betaxolol or adaprolol. It should be noted that surprisingly, this reduced irritation was observed even with preparations which did not contain any drug.

Examples 14–15: Increased Bioavailability

The bioavailability of compositions formulated in accordance with the invention was compared to that of aqueous ophthalmic drug formulations in two systems.

Example 14: Miotic Activity of Pilocarpine

Changes in pupil diameter were measured at 30 min intervals in 10 rabbits following treatment with one 50 μl drop of different pilocarpine formulations.

The maximum Reduction in Pupil Diameter (max. RPD) and the Area Under the Curve (AUC) of the RPD/time curve were used to quantify the miotic activity. Results are shown below in Table 3.

TABLE 3

| Formulation | max. RPD (mm) | AUC (mm × hr) |
| --- | --- | --- |
| 2% pilocarpine nitrate (Lab. H. Faure, France) | −1.7 ± 0.5 | 2.9 ± 1.2 |
| 2% pilocarpine HCl (Example 2) | −2.1 ± 0.6 | 4.3 ± 1.5 |

Mean ± SD, n = 10

The pilocarpine composition of Example 2 of the invention showed a significantly higher (P<0.05) miotic activity as compared commercially available pilocarpine formulation.

Example 15: Ocular Permeability of Indomethacin

Indomethacin is a synthetic non-steroid anti-inflammatory drug. It is practically insoluble in water and although soluble in alkaline solutions, it is unstable under these conditions. Interest in the use of indomethacin in ophthalmology has fluctuated through the years. It is currently available as 1% suspension (INDOPTIC, Merck, Sharp & Dohme) used in conjunction with cataract surgery.

Anterior aqueous humor drug levels ($C_a$) of indomethacin were measured in albino rabbits, following topical treatment with 1 drop (50 μl) of: a) INDOPTIC (1% suspension); b) 0.2% Indomethacin (Example 11); and c) 0.4% Indomethacin (Example 10). The results are presented below in Table 4.

TABLE 4

| | Anterior Chamber Concentration (μM) | | |
| --- | --- | --- | --- |
| Time (hrs) | 1% INDOPTIC Solution | 0.2% Indomethacin (Example 11) | 0.4% Indomethacin (Example 10) |
| 0.5 | 2.2 ± 1.7 (7) | 1.1 ± 0.1 (7) | 1.4 ± 0.9 (6) |
| 1 | 1.0 ± 0.5 (6) | 0.9 ± 0.3 (7) | 2.5 ± 0.9 (6) |
| 3 | 0.6 ± 0.3 (6) | 0.3 ± 0.1 (4) | 1.1 ± 0.4 (6) |

Mean ± SD. Number of eyes in parenthesis.

Aqueous humor indomethacin levels in the INDOPTIC solution treated eyes were up to two-fold higher than those measured in the 0.2% indomethacin (Example 11) treated eyes. This difference between these treatments was not statistically significant, and is smaller than the 5-fold difference between the concentration of indomethacin in the two formulations (0.2% vs. 1%). The 0.4% indomethacin (Example 10) treatment yielded $C_a$ levels even higher than the 1% INDOPTIC solution at 1 hr.

The area under the curve for 0.2% Indomethacin (Example 11) was 2.2 times larger than that of the 1% INDOPTIC solution despite the higher concentration of indomethacin in the latter. Maximum irritation following one drop, four times a day for five days of 0.4% Indomethacin (Example 10) was significantly lower than INDOPTIC (0.4±0.1 vs. 1.1±0.2, respectively, p<0.05). Thus, a higher bioavailability of the drug is obtained for the compositions of the invention while at the same time greatly reduced irritation is achieved.

Examples 16–17

The physical and chemical stability of the compositions of the invention were tested on a range of formulations including various active drugs, surfactant types and concentrations, and other excipients such as preservatives and anti-oxidants.

Example 16

The pilocarpine composition of Example 2 was studied for 6 months at four different temperatures: 4° C., 28° C., 37° C. and 45° C. There was no change in the drug content even at the higher test temperatures. It is worth noting that 6 months at 45° C. is equivalent to 2–3 years at room temperature. The droplet size measured after 3 months at 45° C. was 122±30 nm, as compared to 102±31 nm at the time of production. Visual observations are made to assess color, creaming and oil separation, and these were found to be acceptable. The phospholipid oxidation was less than 0.3% measured by the tetrabarbituric acid method described in Liposome Technology, 2nd edition (1992) Gregoriadis, ed., CRS Press Inc., Boca Raton, Fla. pp 501–527.

Example 17

The adaprolol compositions of Examples 6–8 were subjected to accelerated stability measurements after two months at 45° C. For each composition, the drug content after two months dropped to 96% of the label content. There was no pronounced change in the droplet size which stayed at 120±38 nm. In the composition of Example 7, the pH dropped from 6 to 5.4 which is reasonable under these conditions. Visual observations of the emulsion properties were acceptable, and there was only minor phospholipid oxidation.

Example 18

A dose response following a single administration of the composition was carried out on adult male albino rabbits weighing about 3.0–3.5 kg. Two groups of rabbits were used for comparing the effect of pilocarpine administered in either a generic composition (comprising pilocarpine hydrochloride in aqueous buffer at about pH 5) or with the TYLOXOPOL emulsion of Example 2. The compositions were administered to the right eye of the rabbits following three days' measurement of baseline IOP which was performed in order to observe the health of the eye as well as to establish a baseline IOP for each animal.

The intraocular pressure in the eye was measured using a Langum pneumatic tonometer with a floating tip sensor. The sensor pressure was measured with a Sanborn recorder. The tonometer was standardized every day against a pressurized Silastic membrane. For IOP measurement, one drop of the local anesthetic Benoximate HCl (Fisher Laboratories, Israel) diluted three-fold in a sterile saline solution, was instilled into each eye.

In this study, the baseline IOP was measured on the day preceding the administration of pilocarpine at specific times: 8:00, 9:00, 11:00, 13:00, 15:00, 18:00 hours. The tested preparation was then applied to the right eye and the left eye was left untreated. IOP was then measured in the treated and the contralateral eyes, which measurements were taken on the same day and during the next day at the same time at which the baseline IOP curve was taken.

Figure 1:
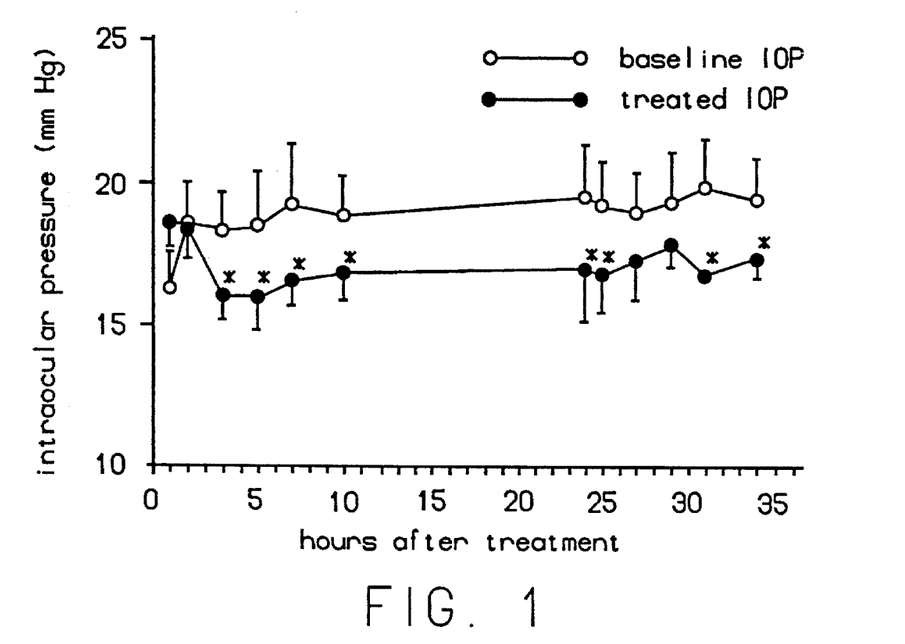
FIG. 1 shows the baseline intraocular pressure ("IOP") in eyes of rabbits and the IOP following administration of a pilocarpine containing emulsion which includes the non-ionic surfactant TYLOXAPOL.

As can be seen in FIG. 1, a single dose of the TYLOXAPOL emulsion of Example 2 caused a decrease in IOP levels which persisted throughout the entire tested period. The maximal change in IOP reduction obtained by a single dose of this emulsion was 16% and was noted at 24 and 34 hours after administration.

Figure 2:
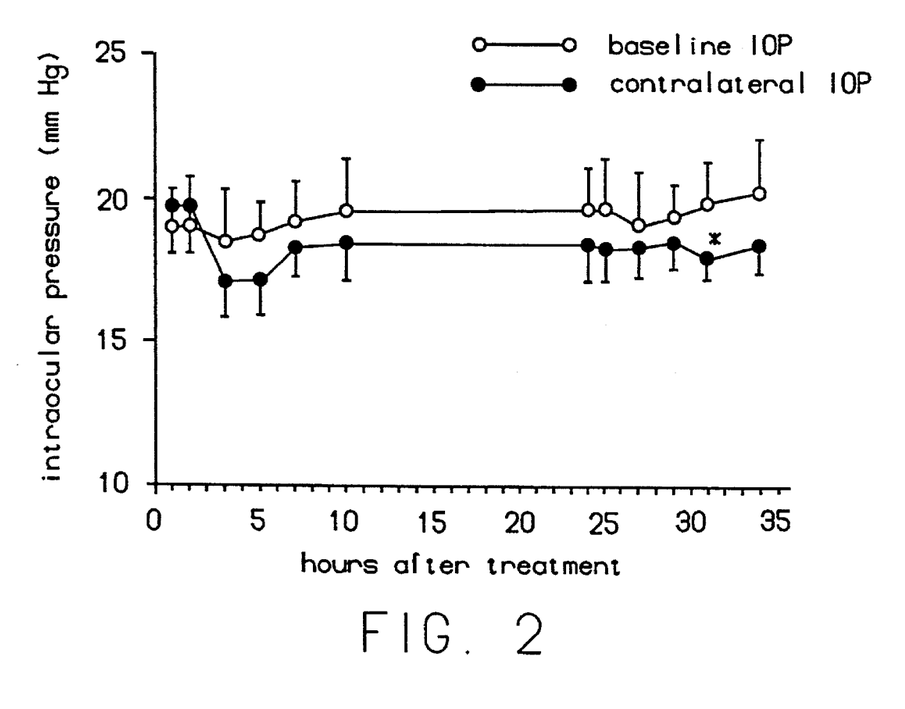
FIG. 2 shows the IOP results from the contralateral eyes of the rabbits which received the pilocarpine emulsion as per FIG. 1.

The results from the contralateral eye are shown in FIG. 2, and as can be seen there was also some reduction in IOP, although less statistically significant (p>0.05). The maximal reducing effect did not exceed 1.9 mmHg (a decrease of about 10%) which occurred at 31 and 34 hours after administration.

Example 19

A study on the clinical affects of the 2% pilocarpine emulsion of Example 2 was made. The study was performed on 20 young healthy volunteers, each receiving a single topical dose in the right eye of either the 2% pilocarpine microemulsion or of a placebo containing the microemulsion alone. The parameters that were measured in each case were IOP and a decrease of the pupil diameter (miosis).

Figure 3:
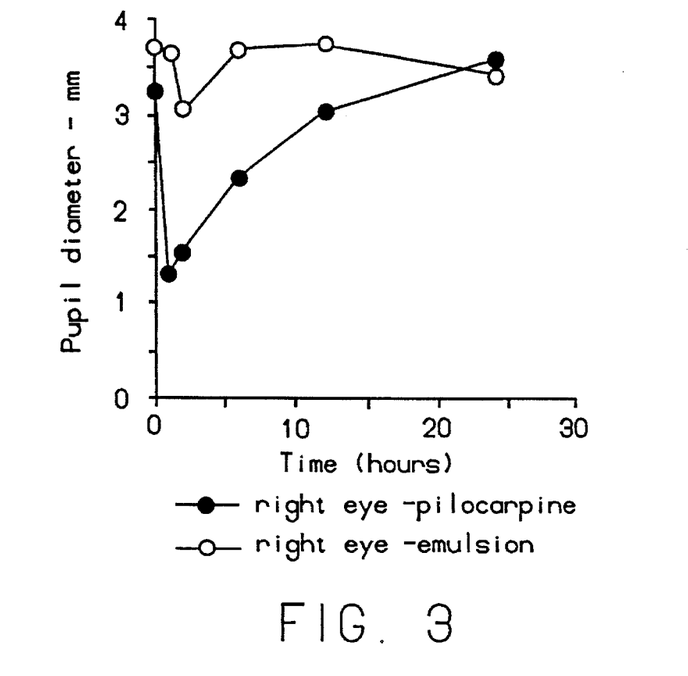
FIG. 3 shows miosis in an eye of human subjects following treatment with a 2% pilocarpine emulsion composition compared to the same emulsion without pilocarpine.
Figure 4:
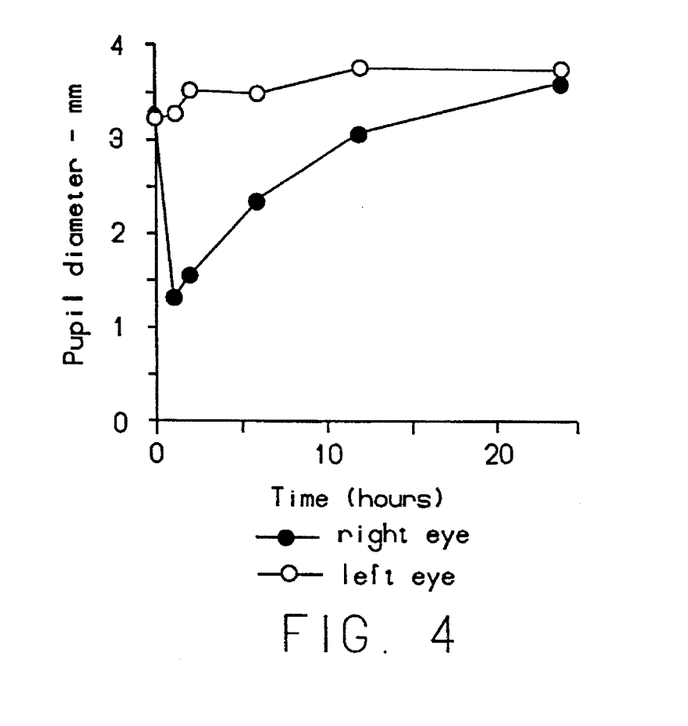
FIG. 4 shows miosis in the contralateral eye of human subjects following treatment with a 2% pilocarpine emulsion composition compared to the same emulsion without pilocarpine, as per FIG. 3.

Miosis was observed in the treated eyes upon addition of the drug although measurements were made only 1 hr following administration. The results, presented in FIG. 3 show that the pilocarpine effect is dramatic both as compared to the placebo application and to the effect in the contralateral eye. As can be seen, the diameter of the pupil prior to administration which was measured to be about 3.5 mm (standard error of mean (SE)=0.2, n=38), decreased within 1 hr to about 1.3 mm (SE=0.1, n=10). After about 12 hrs the normal size of the pupil was regained. This data is presented as the change in IOP vs. time in FIG. 4.

Figure 5:
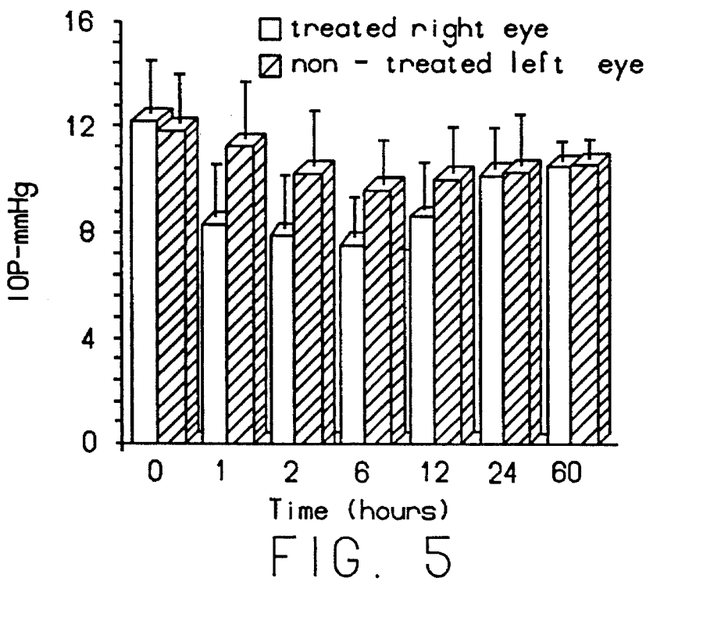
FIG. 5 shows the IOP in human subjects following administration of a 2% pilocarpine containing emulsion versus baseline in both treated and contralateral eyes with a comparison to the administration of the same emulsion without pilocarpine.
Figure 6:
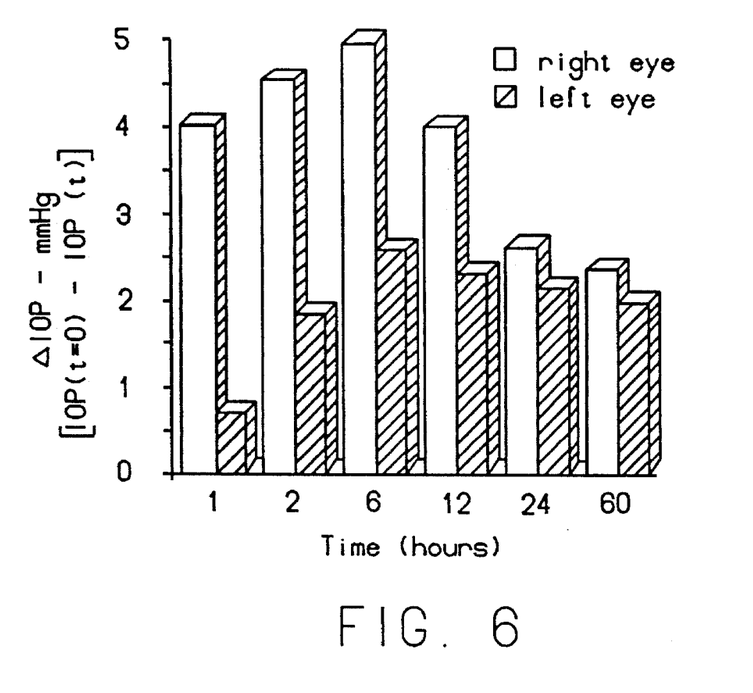
FIG. 6 shows the change in IOP versus baseline level in human subjects following administration of a 2% pilocarpine containing emulsion versus for both treated and contralateral eyes with a comparison to the administration of the same emulsion without pilocarpine.

Intraocular pressure was measured after 1 hr in all 40 eyes (of the 20 volunteers). As can be seen in FIGS. 5 and 6, the IOP decreased from 12.1 mmHg (SE=0.4, n=20) prior to administration of the drug, to 8.2 (SE=0.6, n=10) 1 hr after administration and to 7.4 (SE=0.5, n=10) after 6 hrs. IOP was maintained at about 8.3 mmHg (SE=0.6) for up to 12 hrs. The IOP returned to normal level after about 24 hrs.

As can further be seen in FIGS. 5 and 6, the IOP dropped also in the untreated (left eye) which likely occurs as a result of a systemic reaction. As a control, the emulsion of Example 1 was administered in a similar manner, and no significant change in IOP was measured.

What is claimed is:

1. An ocular drug delivery vehicle of an oil-in-water submicron emulsion consisting essentially of about 0.5 to 50% of a first component of an oil, about 0.1 to 10% of a second component of an emulsifier, comprising a phospholipid, about 0.05 to 5% of a non-ionic surfactant and an aqueous component, said submicron emulsion having a mean droplet size in the range of 0.05 to 0.5 μm, and a weight ratio of surfactant to oil of about 1:1 or less.

2. The vehicle of claim 1 wherein the mean droplet size is between about 0.1 and 0.3 μm.

3. The vehicle of claim 1 wherein the first component is a medium chain triglyceride oil, a vegetable oil, a mineral oil or mixtures thereof.

4. The vehicle of claim 3 wherein the first component is present in an amount of about 1 to 20%.

5. The vehicle of claim 3 wherein the first component is present in an amount of about 30 to 50% to form a viscous composition.

6. The vehicle of claim 1 wherein the phospholipid is lecithin, phosphatidylcholine, phosphatidylethanolamine or mixtures thereof.

7. The vehicle of claim 1 wherein the emulsifier is present in an amount of about 0.2 to 5%.

8. The vehicle of claim 1 wherein the surfactant is a non-ionic alkylene oxide condensate of an organic compound which contains one or more hydroxyl groups.

9. The vehicle of claim 8 wherein the surfactant is an ethoxylated alcohol or ester compound.

10. The vehicle of claim 9 wherein the non-ionic surfactant is present in an amount of about 0.2 to 5%.

11. The vehicle of claim 1 wherein the first component is present in an amount of about 1 to 20%, and the second component and the ionic surfactant are each present in an amount of about 0.2 to 1% so that the weight ratio of surfactant to oil is about 1:1 to about 1:100.

12. A topical ophthalmic composition comprising an effective amount of an ophthalmic drug and an ocular drug delivery vehicle consisting essentially of about 0.5 to 50% of a first component of an oil, about 0.1 to 10% of a second component of an emulsifier, comprising a phospholipid, about 0.05 to 5% of a non-ionic surfactant and an aqueous component, said submicron emulsion having a mean droplet size in the range of 0.05 to 0.5 μm, and a weight ratio of surfactant to oil of about 1:1 or less.

13. The composition of claim 12 wherein the drug is an anti-glaucoma drug, beta adrenergic blocker or other autonomic system drug, a local anesthetic, asteroid, a non-steroidal anti-inflammatory drug, an antibiotic drug, an antifungal drug, an antiviral drug or combinations thereof.

14. The composition of claim 12 wherein the drug is hydrophilic or amphiphilic.

15. The composition of claim 13 wherein the drug is pilocarpine or timolol.

16. The composition of claim 12 wherein the drug is hydrophobic.

17. The composition of claim 16 wherein the drug is indomethacin, betaxolol or adaprolol.

18. The composition of claim 12 wherein the drug is present in an amount of about 0.05 to 5% by weight.

19. The composition of claim 12 further comprising a preservative, an antioxidant or an osmotic agent.

20. The composition of claim 12 further comprising an effective amount of an additional drug.

21. The composition of claim 20 wherein the additional drug is a β-adrenergic blocker, a cannabinoid, a cholinesterase inhibitor, a sympathomimetic or a carbonic anhydrase inhibitor.

22. The composition of claim 15 wherein the ophthalmic drug includes an effective amount of the combination of a first ophthalmic drug and a second drug which decreases intraocular pressure when administered to the eye of a patient.

23. A method for reducing eye irritation induced by the administration of a drug, which comprises administering said drug to the eye together with the ocular drug delivery vehicle of claim 1.

24. The method of claim 23 which further comprises selecting the emulsion to have droplets of a mean diameter of between about 0.1 and 0.3 μm.

25. A method for reducing eye irritation which comprises administering to an irritated eye an effective amount of the ocular drug delivery vehicle of claim 1.

26. The method of claim 25 which further comprises selecting the emulsion to have droplets of a mean diameter of between about 0.1 and 0.3 μm.

27. A method for administering a topical ophthalmic composition of a drug having a therapeutic effect on the eye, which comprises formulating the topical ophthalmic composition of claim 12 and administering an effective amount of such composition to the eye of a patient.

28. The method of claim 27 which further comprises selecting the emulsion to have droplets of a mean diameter of between about 0.1 and 0.3 μm.

29. A method for administering increased amount of a drug to the eye without causing irritation thereof, which comprises administering said increased amount of said drug to the eye with the ocular drug delivery vehicle of claim 1.

30. The method of claim 29 which further comprises selecting the emulsion to have droplets of a mean diameter of between about 0.1 and 0.3 μm.

31. A method for administering increased amount of a drug to the eye without causing irritation thereof, which comprises administering said increased amount of said drug to the eye in the composition of claim 12.

32. The method of claim 31 which further comprises selecting the emulsion to have droplets of a mean diameter of between about 0.1 and 0.3 μm.

33. A method for providing increased bioavailability of an ophthalmic drug which comprises administering said drug to the eye in the composition of claim 12.

34. The method of claim 33 which further comprises selecting the emulsion to have droplets of a mean diameter of between about 0.1 and 0.3 μm.

35. A method for providing increased bioavailability of an ophthalmic drug which comprises administering said drug to the eye with the ocular drug delivery vehicle of claim 1.

36. The method of claim 35 which further comprises selecting the emulsion to have droplets of a mean diameter of between about 0.1 and 0.3 μm.

37. The method of claim 28 wherein the drug is pilocarpine or timolol.

* * * * *